(12) United States Patent
Fitzsimmons et al.

(10) Patent No.: US 10,884,384 B2
(45) Date of Patent: Jan. 5, 2021

(54) SYSTEMS AND METHODS FOR DETERMINING AN END OF LIFE STATE FOR SURGICAL DEVICES

(71) Applicant: Covidien LP, Mansfield, MA (US)

(72) Inventors: Thomas Fitzsimmons, New Milford, CT (US); Michelle Grasso, Shelton, CT (US); Michael Ingmanson, Stratford, CT (US); Michael Zemlok, Prospect, CT (US)

(73) Assignee: COVIDIEN LP, Mansfield, MA (US)

( * ) Notice: Subject to any disclaimer, the term of this patent is extended or adjusted under 35 U.S.C. 154(b) by 143 days.

(21) Appl. No.: 16/173,421

(22) Filed: Oct. 29, 2018

(65) Prior Publication Data

US 2019/0064758 A1  Feb. 28, 2019

Related U.S. Application Data

(62) Division of application No. 14/521,752, filed on Oct. 23, 2014, now Pat. No. 10,133,248.
(Continued)

(51) Int. Cl.
*A61B 17/072* (2006.01)
*G05B 15/02* (2006.01)
(Continued)

(52) U.S. Cl.
CPC ........ *G05B 15/02* (2013.01); *A61B 17/07207* (2013.01); *G01M 99/005* (2013.01);
(Continued)

(58) Field of Classification Search
CPC .......... A61B 2017/00132; A61B 2017/00017; A61B 17/072
(Continued)

(56) References Cited

U.S. PATENT DOCUMENTS 3,572,447 A  3/1971  Pauley
6,016,448 A  1/2000  Busacker et al.
(Continued)

FOREIGN PATENT DOCUMENTS

CN  1662174 A  8/2005
JP  05049647  3/1993
(Continued)

OTHER PUBLICATIONS

Japanese Office Action corresponding to counterpart Patent Application No. JP 2014-264805 dated Dec. 20, 2018.
(Continued)

*Primary Examiner* — Gloria R Weeks (57) ABSTRACT

The present disclosure is directed to systems and methods for determining an end of life state for an electromechanical surgical system. The system includes an end effector configured to perform at least one function and a shaft assembly being arranged for selectively interconnecting the end effector and a hand-held surgical instrument. The hand-held surgical instrument includes an instrument housing defining a connecting portion for selectively connecting with the shaft assembly. The hand-held surgical instrument also includes a motor assembly, a sensor array configured to obtain an operational parameter of the hand-held surgical instrument, and a controller configured to control operation of the hand-held surgical instrument based on the operational parameter obtained by the sensor array.

6 Claims, 8 Drawing Sheets

Related U.S. Application Data (60) Provisional application No. 61/985,081, filed on Apr. 28, 2014.

(51) Int. Cl.
*G01M 99/00* (2011.01)
*A61B 17/00* (2006.01)
*A61B 17/29* (2006.01)

(52) U.S. Cl.
CPC ..... *A61B 17/29* (2013.01); *A61B 2017/00017* (2013.01); *A61B 2017/00026* (2013.01); *A61B 2017/0046* (2013.01); *A61B 2017/00084* (2013.01); *A61B 2017/00106* (2013.01); *A61B 2017/00115* (2013.01); *A61B 2017/00123* (2013.01); *A61B 2017/00221* (2013.01); *A61B 2017/00398* (2013.01); *A61B 2017/00473* (2013.01)

(58) Field of Classification Search
USPC .......................................................... 227/2
See application file for complete search history.

(56) References Cited

U.S. PATENT DOCUMENTS

| | | | |
|---|---|---|---|
| 6,981,941 B2 | 1/2006 | Whitman et al. | |
| 7,025,774 B2 | 4/2006 | Freeman | |
| 7,118,564 B2 | 10/2006 | Ritchie et al. | |
| 7,784,663 B2 | 8/2010 | Shelton, IV | |
| 7,972,328 B2 * | 7/2011 | Wham | A61B 18/1206 606/34 |
| 8,012,170 B2 | 9/2011 | Whitman et al. | |
| 8,118,206 B2 | 2/2012 | Zand et al. | |
| 8,525,687 B2 | 9/2013 | Tran | |
| 8,556,152 B2 | 10/2013 | Marczyk et al. | |
| 8,627,993 B2 | 1/2014 | Smith | |
| 8,695,866 B2 | 4/2014 | Leimbach et al. | |
| 8,808,311 B2 * | 8/2014 | Heinrich | A61B 17/0469 606/142 |
| 8,967,443 B2 | 3/2015 | McCuen | |
| 9,226,766 B2 * | 1/2016 | Aldridge | H04L 25/4902 |
| 9,936,961 B2 | 4/2018 | Chien | |
| 10,133,248 B2 | 11/2018 | Fitzsimmons et al. | |
| 2005/0113815 A1 | 5/2005 | Ritchie et al. | |
| 2005/0116673 A1 | 6/2005 | Carl et al. | |
| 2007/0035203 A1 | 2/2007 | Bromfield | |
| 2011/0121049 A1 | 5/2011 | Malinouskas et al. | |
| 2012/0143211 A1 | 6/2012 | Kishi | |
| 2013/0193898 A1 | 8/2013 | Williams et al. | |
| 2013/0219725 A1 | 8/2013 | Winkel | |
| 2014/0110453 A1 | 4/2014 | Wingardner et al. | |
| 2016/0249915 A1 | 9/2016 | Beckman et al. | |
| 2016/0249916 A1 | 9/2016 | Shelton, IV et al. | |
| 2016/0249917 A1 | 9/2016 | Beckman | |
| 2018/0092659 A1 | 4/2018 | Kim | |

FOREIGN PATENT DOCUMENTS

| | | |
|---|---|---|
| JP | H0549647 A | 3/1993 |
| JP | H10290810 A | 11/1998 |
| JP | 2008546503 A | 12/2008 |
| JP | 2014083440 A | 5/2014 |
| WO | 2007002180 A2 | 1/2007 |
| WO | 2009039506 A1 | 3/2009 |

OTHER PUBLICATIONS

European Office Action corresponding to counterpart Int'l Appln. No. EP 14 19 9657.9 dated Jun. 9, 2016.
European Search Report dated Jul. 21, 2015, issued in European Application No. 14 19 9657.
Japanese Office Action dated Aug. 27, 2018 in corresponding Japanese Patent Application No. 2014-264805, with English translation.
CN Office Action dated Jul. 4, 2018 in corresponding CN Patent Application No. 201410855808.8 together with English translation.
Japanese Notice of Allowance corresponding to counterpart Patent Application JP 2014-264805 dated Apr. 25, 2019; and machine generated English Translation.
Australian Examination Report No. 1 issued in Patent Application AU 2014265007 dated Jan. 25, 2019.

* cited by examiner

SYSTEMS AND METHODS FOR DETERMINING AN END OF LIFE STATE FOR SURGICAL DEVICES

CROSS-REFERENCE TO RELATED APPLICATIONS

The present application is a Divisional application claiming the benefit of and priority to U.S. patent application Ser. No. 14/521,752, filed on Oct. 23, 2014, which claims the benefit of and priority to U.S. Provisional Application Ser. No. 61/985,081, filed on Apr. 28, 2014, the entire content of each of which being incorporated herein by reference.

BACKGROUND

1. Technical Field

The present disclosure relates to surgical apparatus, devices and/or systems for performing minimally invasive surgical procedures and methods of use thereof. More specifically, the present disclosure relates to systems and methods for determining an end of life state for electromechanical, hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. Some electromechanical surgical devices include a handle assembly, which is reusable, and replaceable loading units and/or single use loading units or the like that are selectively connected to the handle assembly prior to use and then disconnected from the handle assembly following use, in order to be disposed of or in some instances sterilized for re-use.

Typically, electromechanical surgical devices have an end of life that is predetermined during the engineering development phase and hard set within each device that is sold. Thus, all the devices have an identical lifespan regardless of factors which may reduce or prolong useful life of the device.

Accordingly, a need exists for determining an end of life state for electromechanical surgical apparatus, devices and/or systems in order to reduce or prolong the useful life of the device.

SUMMARY

In embodiments of the present disclosure, an electromechanical surgical system is provided. The system includes an end effector configured to perform at least one function and a shaft assembly being arranged for selectively interconnecting the end effector and a hand-held surgical instrument. The hand-held surgical instrument includes an instrument housing defining a connecting portion for selectively connecting with the shaft assembly. The hand-held surgical instrument also includes a motor assembly, a sensor array configured to obtain an acoustic metric or electrical metric of the hand-held surgical instrument, and a controller configured to control operation of the hand-held surgical instrument based on the acoustic metric or electrical metric obtained by the sensor array.

In some aspects, the hand-held surgical instrument includes a transceiver configured to communicate with an external device. The external device is a charging device, a local server, or an external server. The hand-held surgical instrument may communicate with the charging device, the local server, or the external server via a cloud.

In some aspects, the sensor array includes at least one acoustic sensor, temperature sensor, voltage sensor, current sensor, or vibration sensor.

In another embodiment of the present disclosure, an end of life state determination method for a hand-held surgical instrument is provided. The method includes obtaining at least one acoustic or electrical metric of the hand-held surgical instrument. The method also includes comparing the at least one acoustic or electrical metric to a threshold value and disabling the hand-held surgical instrument when the at least one acoustic or electrical metric is greater than the threshold value.

In some aspects, the method further includes presetting the threshold value by a manufacturer. In other aspects, the method further includes setting the threshold value as a function of a measured characteristic. In yet other aspects, the method further includes adjusting the threshold value as a function of continually aggregated field data. The continually aggregated field data is at least one of device performance, geographical metrics, hospital condition metrics, clinician metrics, regional based performance metrics, geographic based performance metrics, or time zone based performance metrics.

In yet another embodiment of the present disclosure, an end of life state prolonging method for a hand-held surgical instrument is provided. The method includes obtaining at least one operational parameter of the hand-held surgical instrument. The method also includes comparing the at least one operational parameter to a predetermined threshold value and determining that a device parameter of the hand-held surgical instrument can be augmented when the at least one operational parameter is greater than the predetermined threshold value. When the device parameter can be augmented, the method also includes augmenting the device parameter of the hand-held surgical instrument.

In some aspects, the hand-held surgical instrument is disabled if the device parameter of the hand-held surgical instrument cannot be augmented.

In some aspects, the method further includes setting the threshold value by a manufacturer. In other aspects, the method further includes setting the threshold value as a function of a measured characteristic during manufacturing. In yet other aspects, the method further includes setting the threshold value as a function of continually aggregated field data. The continually aggregated field data is at least one of device performance, geographical metrics, hospital condition metrics, clinician metrics, regional based performance metrics, geographic based performance metrics, or time zone based performance metrics.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A or B" means "(A), (B), or (A and B)". For the purposes of this description, a phrase in the form "at least one of A, B, or C" means "(A), (B), (C), (A and B), (A and C), (B and C), or (A, B and C)".

The term "clinician" refers to any medical professional (i.e., doctor, surgeon, nurse, or the like) performing a medical procedure involving the use of embodiments described herein. As shown in the drawings and described throughout the following description, as is traditional when referring to relative positioning on a surgical instrument, the term "proximal" or "trailing" refers to the end of the apparatus which is closer to the clinician and the term "distal" or "leading" refers to the end of the apparatus which is further away from the clinician.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" is any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. For the purposes of this definition, no distinction is made between languages which are interpreted, compiled, or use both compiled and interpreted approaches. For the purposes of this definition, no distinction is made between compiled and source versions of a program. Thus, reference to a program, where the programming language could exist in more than one state (such as source, compiled, object, or linked) is a reference to any and all such states. The definition also encompasses the actual instructions and the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

In embodiments described herein, a powered surgical device collects various forms of data from the device and compares the collected data to a threshold. Based on the comparison, specific actions can be taken with regard to the end of life state of the device. For instance, the collected data may exhibit that the device has prematurely reached its end of life state and prevent use of the device. In other instances, the device may make adjustments to prolong the end of life of the device.

The systems and methods described herein would permit the possibility of extending the life of powered surgical devices. It will also allow any units that exhibit a premature end of life failure to be safely removed prior to use on a patient. The systems may also include wireless capability and can be connected to the cloud in order to transmit information for analysis in real time. Through electronic signature analysis the system may determine that a limited number of procedures are remaining before an end of life state is reached. The system performance as well as any supply requirements may be transmitted to a surgical coordinator via an email, text message, or both. Data collected from the field can be analyzed to determine if there are any premature component failures that may affect other units in the field, allowing manufacturing to be proactive in addressing any possible field issues.

Figure 1:
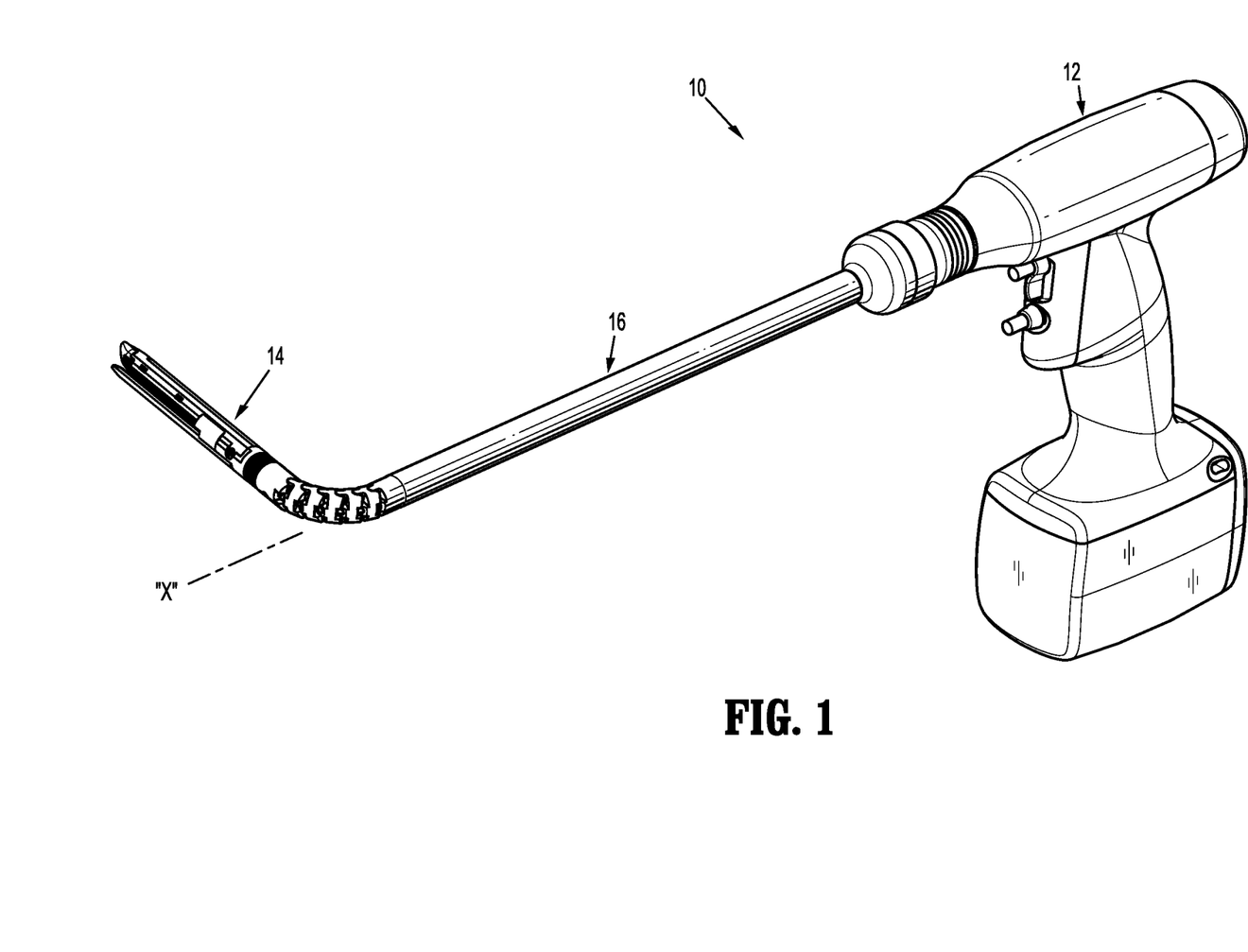
FIG. 1 is a perspective view of an electromechanical surgical system that may incorporate systems or methods in accordance with embodiments of the present disclosure.

Referring initially to FIG. 1, an electromechanical, handheld, powered surgical system, in accordance with embodiments of the present disclosure is shown and generally designated 10. Electromechanical surgical system 10 includes a surgical apparatus or device in the form of an electromechanical, hand-held, powered surgical instrument 12 that is configured for selective attachment thereto of a plurality of different end effectors 14, via a shaft or adapter assembly 16, that are each configured for actuation and manipulation by the electromechanical, hand-held, powered surgical instrument 12. In particular, surgical instrument 12 is configured for selective connection with shaft assembly 16, and, in turn, shaft assembly 16 is configured for selective connection with any one of a plurality of different end effectors 14.

For a detailed description of the construction and operation of exemplary electromechanical, hand-held, powered surgical instrument 12, reference may be made to International Application No. PCT/US2008/077249, filed Sep. 22, 2008 (Inter. Pub. No. WO 2009/039506) and U.S. patent application Ser. No. 12/622,827, filed on Nov. 20, 2009 (U.S. Patent Application Publication No. 2011/0121049), the entire contents of each of which are hereby incorporated herein by reference.

Figure 2:
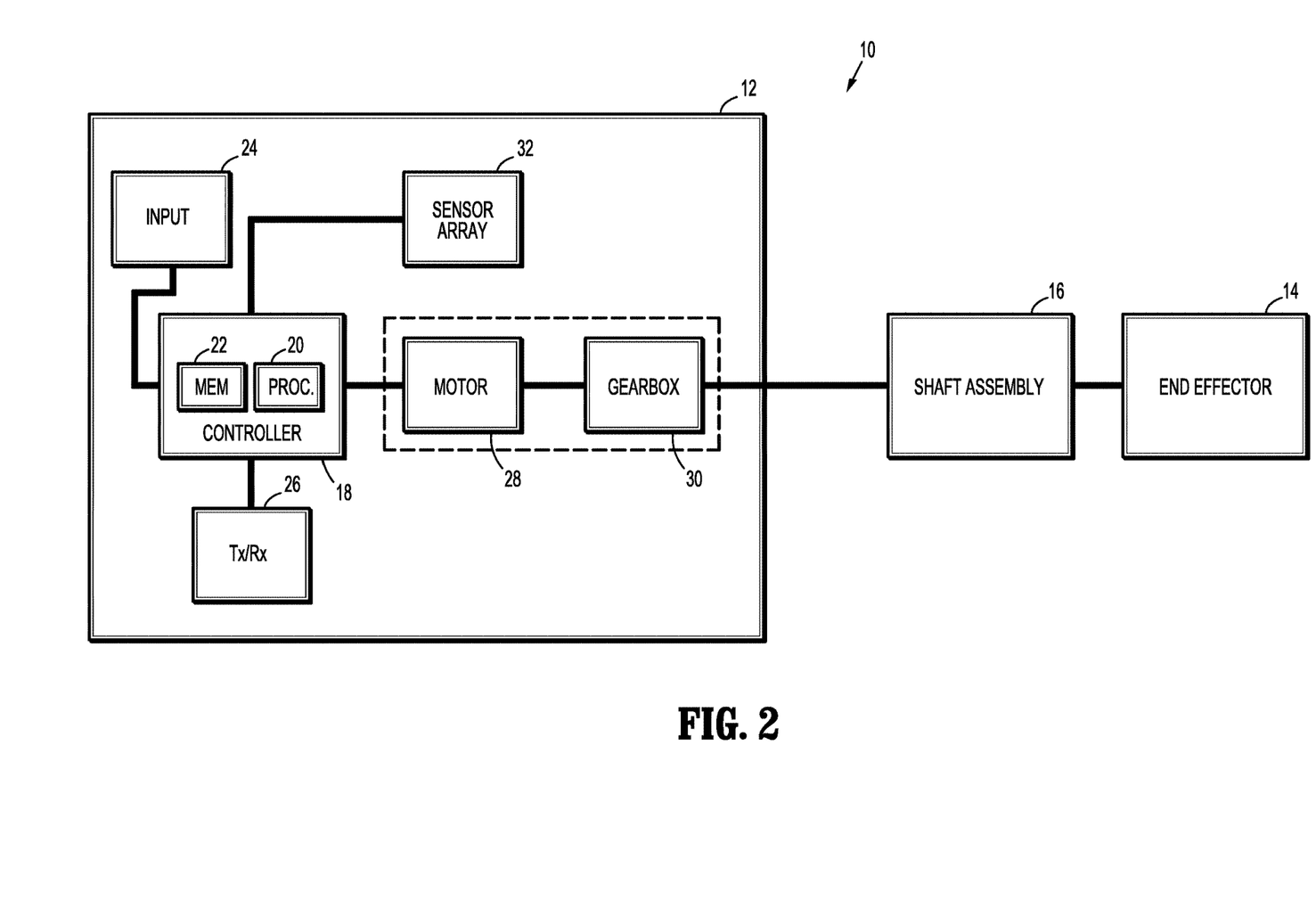
FIG. 2 is a system block diagram of an end of life state determination system in accordance with embodiments of the present disclosure.
Figure 3:
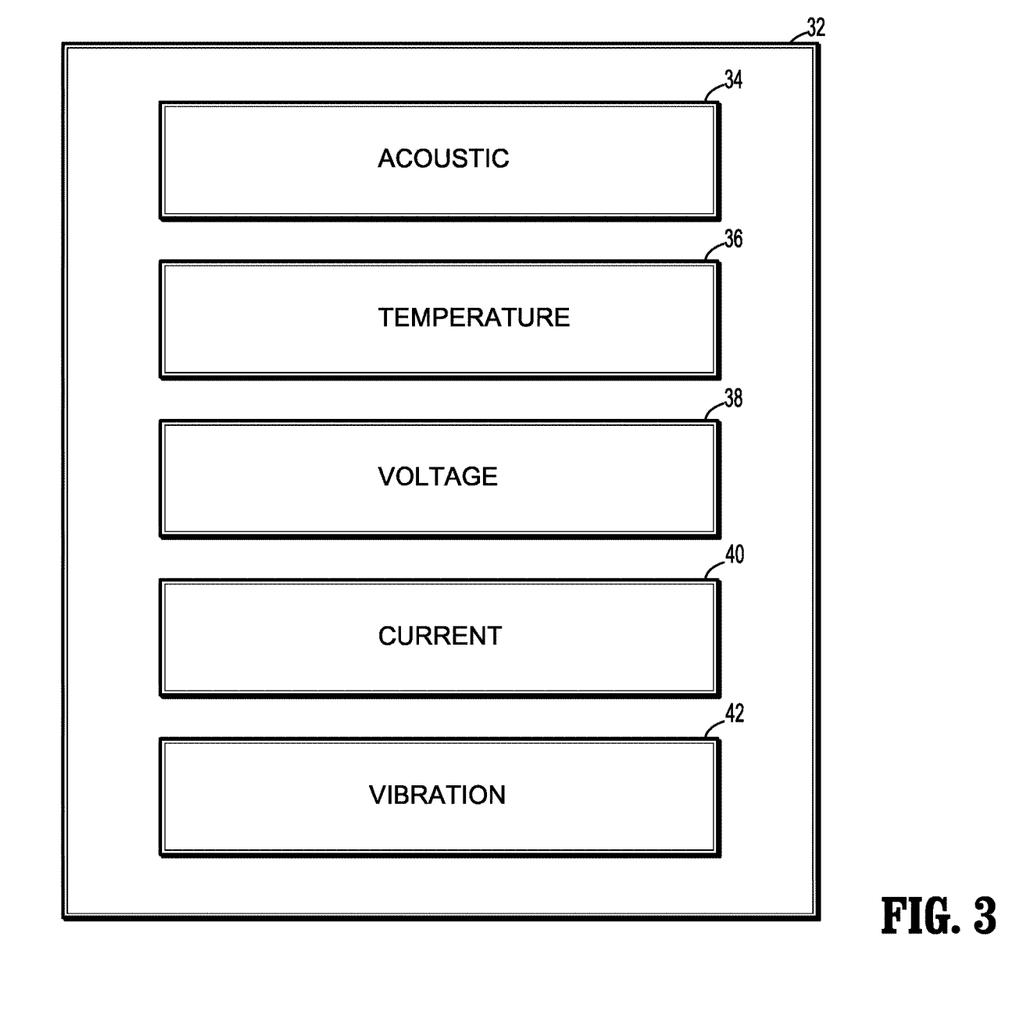
FIG. 3 is a system block diagram of the sensor array of FIG. 2.

FIG. 2 is a system block diagram of an electromechanical, hand-held, powered surgical system, in accordance with embodiments of the present disclosure. As shown in FIG. 2, the powered surgical instrument 12 includes a controller 18 having a central processing unit (CPU) 20 and a memory 22. An input device 24 may include buttons, knobs, switches or the like to control the powered surgical instrument 12. A transceiver 26 transmits and receives data between the powered surgical instrument 12 and an external source as will be described below with reference to FIG. 4. The instrument 12 also has a motor assembly 27 that includes a motor 28 and, in certain embodiments, a gearbox 30. The controller 28 and motor assembly 27 control operation of the shaft assembly 16 and the end effector 14. The powered surgical instrument 12 also includes a sensor array 32 that measures operational parameters, e.g., acoustic based metrics or electrical based metrics, of the instrument 12. As shown in FIG. 3, sensor array 32 may include one or more acoustic sensors 34, temperature sensors 36, voltage sensors 38, current sensors 40, and vibration sensors 42. As will be described in more detail below, the controller 28 controls operation of the powered surgical instrument 12 based on the measured operational parameter provided by the sensor array 32. In some instances, the controller 28 may decide that the powered surgical instrument may or may not be used based on the measured operational parameter. In other instances, the controller 28 may adjust operation of the individual components in the powered surgical instrument 12 during operation of the instrument 12 based on the measured operational parameter.

Figure 4:
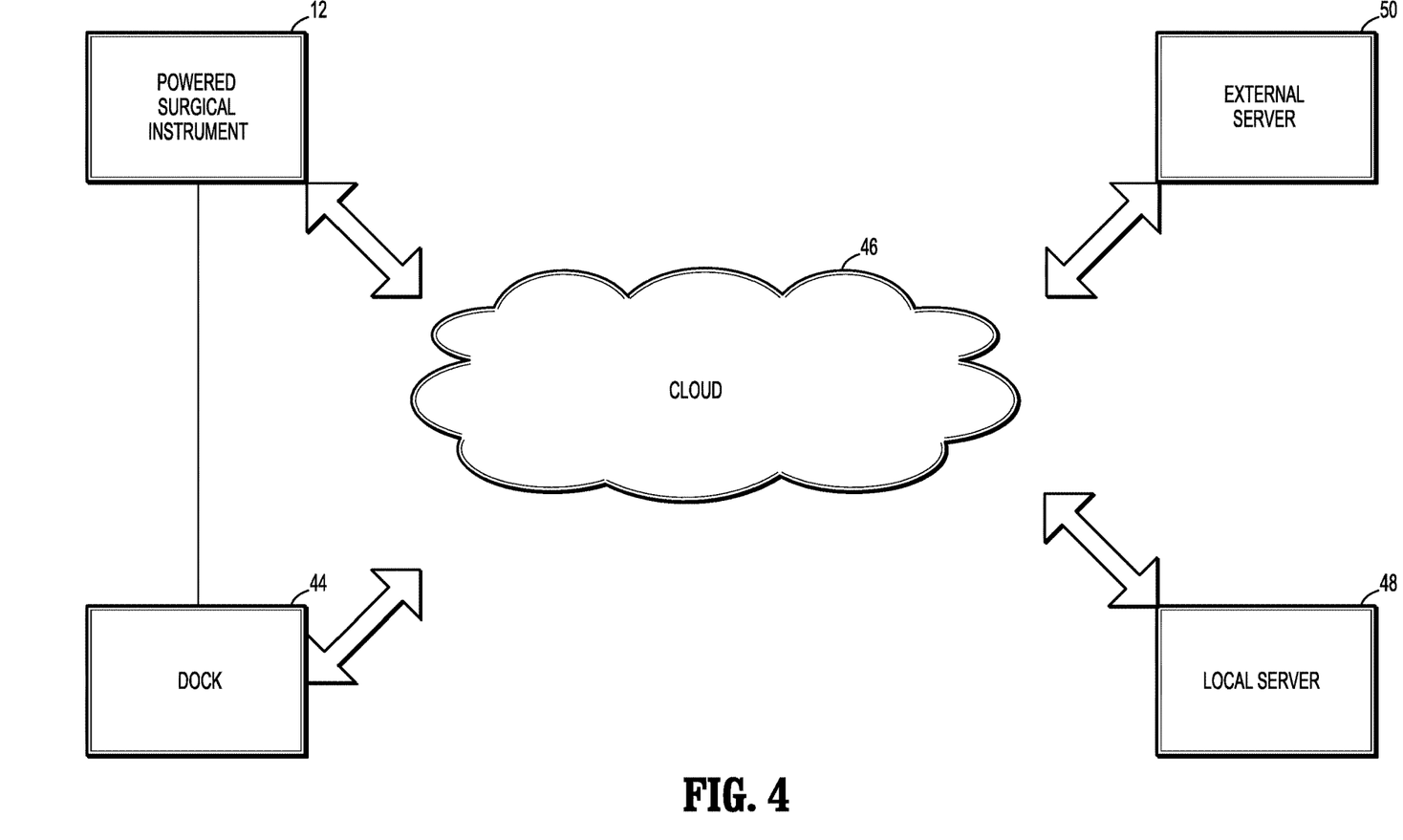
FIG. 4 is a system block diagram of a communication network in accordance with embodiments of the present disclosure.

Referring to FIG. 4, the powered surgical instrument 12 is able to communicate via transceiver 26 with a dock 44. Dock 44 may be a test fixture or a charging device. The instrument 12 may be directly coupled to the dock 44 by a wired connection or instrument 12 may be wirelessly coupled to dock 44 using any known wireless communication method. The instrument 12 and the dock 44 may transmit or receive data from a cloud 46, which is a network of remote servers hosted on the Internet and used to store, manage, or process data in place of local servers or personal computers. A local server 48, e.g., a hospital server, or an external server 50, e.g., a manufacturer's server, may extract data regarding the instrument 12 from the cloud 46 or transmit data to the instrument 12 via the cloud 46.

Referring to FIGS. 1-4, the powered surgical instrument 12 is able to determine, or collect information in order to determine when the instrument 12 will reach the end of life state. In an embodiment of the present disclosure, the sensor array 32 is able to detect vibro-acoustic responses and natural harmonic frequencies of rotational or linear driven electromechanical drive components within the system 10 based on their numerical physical attributes. Such numerical physical attributes include: (i) the number of balls, pins, or needles of any bearings and/or their driven revolutions per minute (RPM); (ii) the number of gear or worm teeth or the mesh frequency of any gears and/or their driven RPM; (iii) the number of radial pins on carriers, number of planets on planetary gear sets of any transmissions and/or their driven RPM; (iv) the number of radial splines or features or universal joints of any couplings and/or their driven RPM; (v) the unsupported beam harmonic frequency range of any linear drives and/or their driven RPM; (vi) the number of armature magnet poles or field slots (based on architecture) of any motors and/or their driven RPM; (vii) the number of radial lobes or features of any cams and/or their driven RPM; (viii) the number of radial features on a cog pulley and/or their driven RPM; and (ix) the number of fan blades or impellers and/or their driven RPM. The above list is meant to merely serve as an example of components within the system 10 that emit a vibro-acoustic response and is not meant to be a complete list of all components within system 10 that emit a vibro-acoustic response.

The sensor array 32 monitors the specific natural harmonic frequencies of the electromechanical drive components to determine the acoustic amplitude limits for a performance degradation and/or reliability confidence threshold for each component. Such acoustic amplitude limits for each specific component within the system 10 can be measured or gauged or assimilated with any form or combination of acoustic or vibration sensors which can include, but are not limited to, accelerometers, electromagnetic inductors, piezoelectric generators, capacitance or electrostatic microphones. Although sensor array 32 has been described as being in the instrument 12, the sensor array may be disposed in the dock 44. During manufacturing, acoustic amplitude limits are stored as threshold values within memory 22. In some embodiments, the threshold values may also be stored in dock 44. During operation of the instrument 12, controller 18 utilizes the stored threshold values to implement any of the following tasks independently or in any combination within the product or subassembly: shut down the device, determine/set specific operational modes, adjust life or use estimations, generate error codes and/or initiate service calls for each specific issue.

In other embodiments, the sensor array 32 monitors electrical properties, e.g., voltage drop or current draw, of various electrical components. The electrical properties are monitored during manufacturing and used to set threshold values that are stored in memory 22. The controller 18 may then monitor the electrical properties of instrument 12 and compare the electrical properties to the stored threshold values to implement any of the following tasks independently or in any combination within the product or subassembly: shut down the device, determine/set specific operational modes, adjust life or use estimations, generate error codes and/or initiate service calls for each specific issue.

Figure 5:
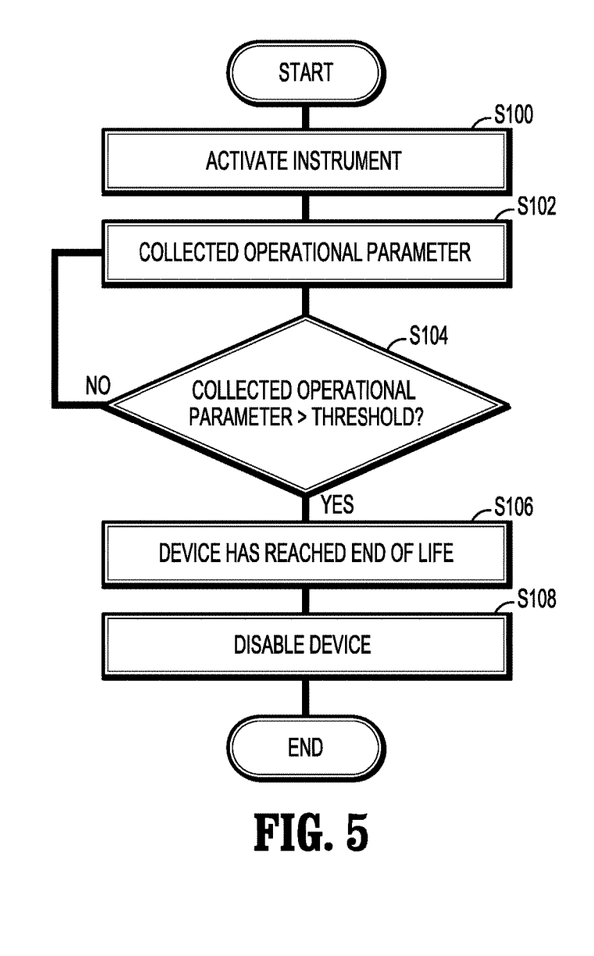
FIG. 5 is a flow chart depicting an end of life state determination method in accordance with embodiments of the present disclosure.

FIG. 5 depicts an end of life state determination method in accordance with an embodiment of the present disclosure. As shown in FIG. 5, the instrument 12 is activated in step s100. In step s102, one or more operational parameters, e.g., acoustic data or electrical data, is collected and compared to a threshold in step s104. If the value of the one ore more operational parameters is less than or equal to the threshold value, the process returns to steps s102 to collect more operational parameters. If the value of the one ore more operational parameters is greater than the threshold value, the process proceeds to step s106 where the controller 18 determines that the instrument 12 has reached the end of life state. Controller 18 then disables the instrument 12 in step s108.

Figure 6:
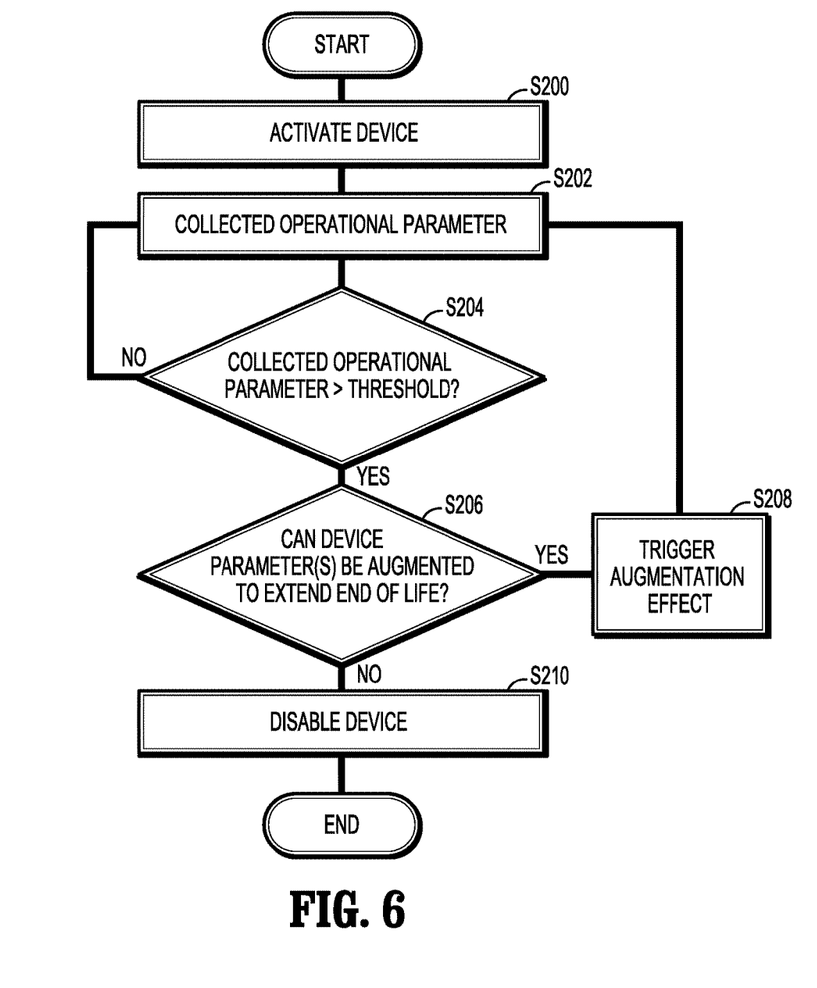
FIG. 6 is a flow chart depicting a method for prolonging the end of life in accordance with embodiments of the present disclosure.
Figure 7:
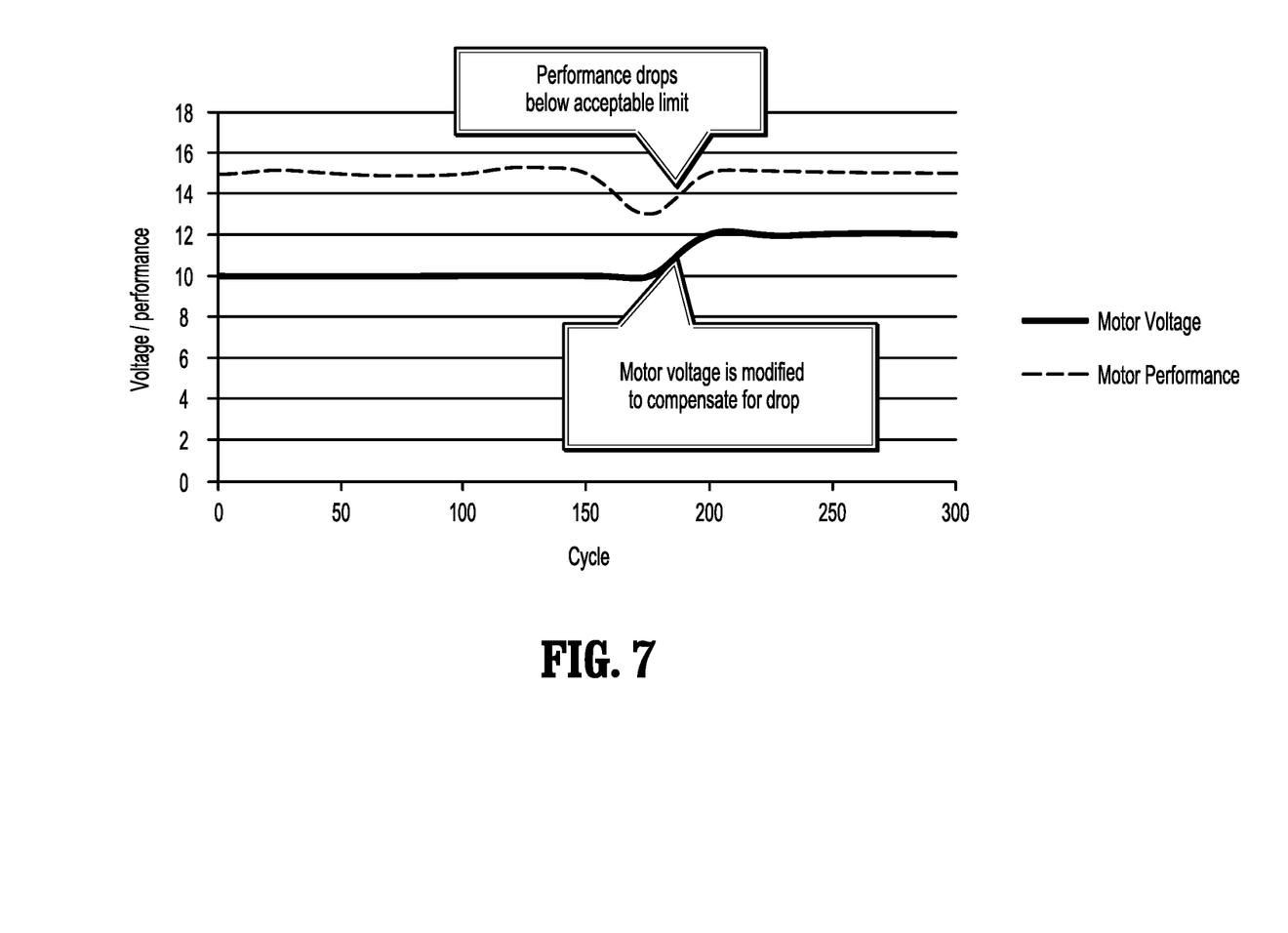
FIG. 7 is a chart depicting an augmentation event for prolonging the end of life of an instrument in accordance with an embodiment of the present disclosure.

FIG. 6 depicts a method for prolonging the end of life in accordance with embodiments of the present disclosure. As shown in FIG. 6, the instrument 12 is activated in step s200. In step s202, one ore more operational parameters, e.g., acoustic data or electrical data, is collected and compared to a threshold in step s204. If the value of the one ore more operational parameters is less than or equal to the threshold value, the process returns to step s202 to collect more operational parameters. If the value of the one ore more operational parameters is greater than the threshold value, the process proceeds to step s206 where the controller 18 determines whether a device parameter or parameters may be augmented to extend the end of life of the instrument 12. For instance, as shown in FIG. 7, the instrument 12 may monitor the performance of the motor 28, e.g., between 150 cycles and 200 cycles, the performance of the motor drops below an acceptable limit. To correct the performance of the motor 28, the voltage supplied to the motor 28 may be increased or augmented to increase the performance of the motor to an acceptable level.

If the controller 18 determines that the device parameter(s) can be augmented, the process proceeds to steps s208 where the instrument 12 triggers the augmentation effect. If the device parameter(s) cannot be altered, the process proceeds to step s210 where the controller 18 disables the device. The controller 18 may determine that the device parameter(s) cannot be altered based on a threshold level, capability of a component to be altered, etc.

The threshold values used in steps s104 and s204 may be set, for example, in one of three ways. In some embodiments, the same threshold values may be set as a static or dynamic limit for all similar devices. In other embodiments, the static or dynamic limit may be set as a function of a measured characteristic during manufacturing or initial calibrations as will be discussed below with regard to FIGS. 8A and 8B. In yet other embodiments, the static or dynamic limit may be set as function of continually aggregated field data as shown in FIG. 9.

Figure 8A:
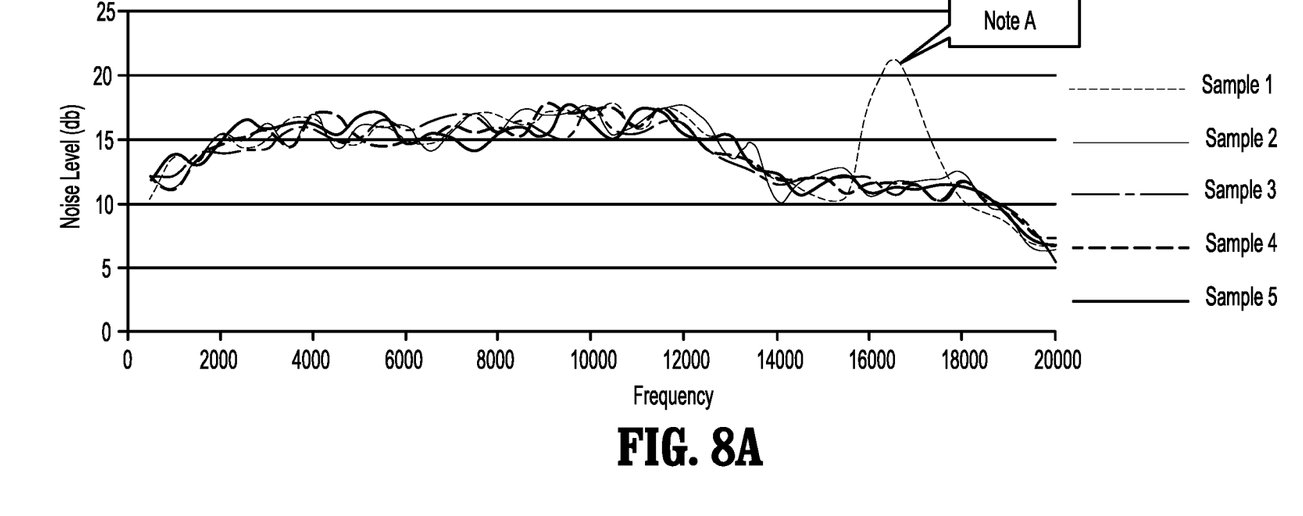
FIG. 8A is a chart and FIG. 8B is a table used to set a threshold value for an instrument in accordance with an embodiment of the present disclosure.
Figure 8B:
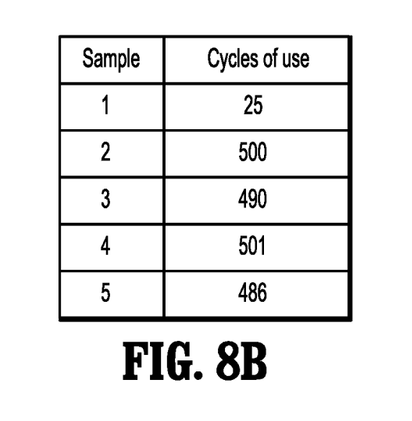

FIGS. 8A and 8B depict an example of the determining an end of life state for a motor that may be used in the instrument 12 during manufacturing or initial calibrations. As shown in FIG. 5A, an acoustic profile for five sample motors are taken initially. The acoustic profile of the five sample motors can be captured by acoustic or vibration sensors. FIG. 5A shows the decibel (dB) level of the five sample motors for each frequency domain between 20 and 20,000 Hz. After the acquisition of the initial acoustic profile, the motors are subjected to end of life testing to determine how long each sample can perform as expected until failure. As shown in FIG. 5B, the five sample motors reach the end of life state after varying number of cycles. For example, sample "1" has been through 25 cycles, sample "2" has been through 500 cycles, sample "3" has been through 490 cycles, sample "4" has been through 501 cycles, and sample "5" has been through 486 cycles. Thus, a conclusion can be drawn that a motor (sample 1) with a high dB level in a specific frequency band (see Note A in FIG. 8A) is likely to fail at a low number of uses. This information may be used to limit use of the instrument in the field or the component may be scrapped altogether.

Figure 9:
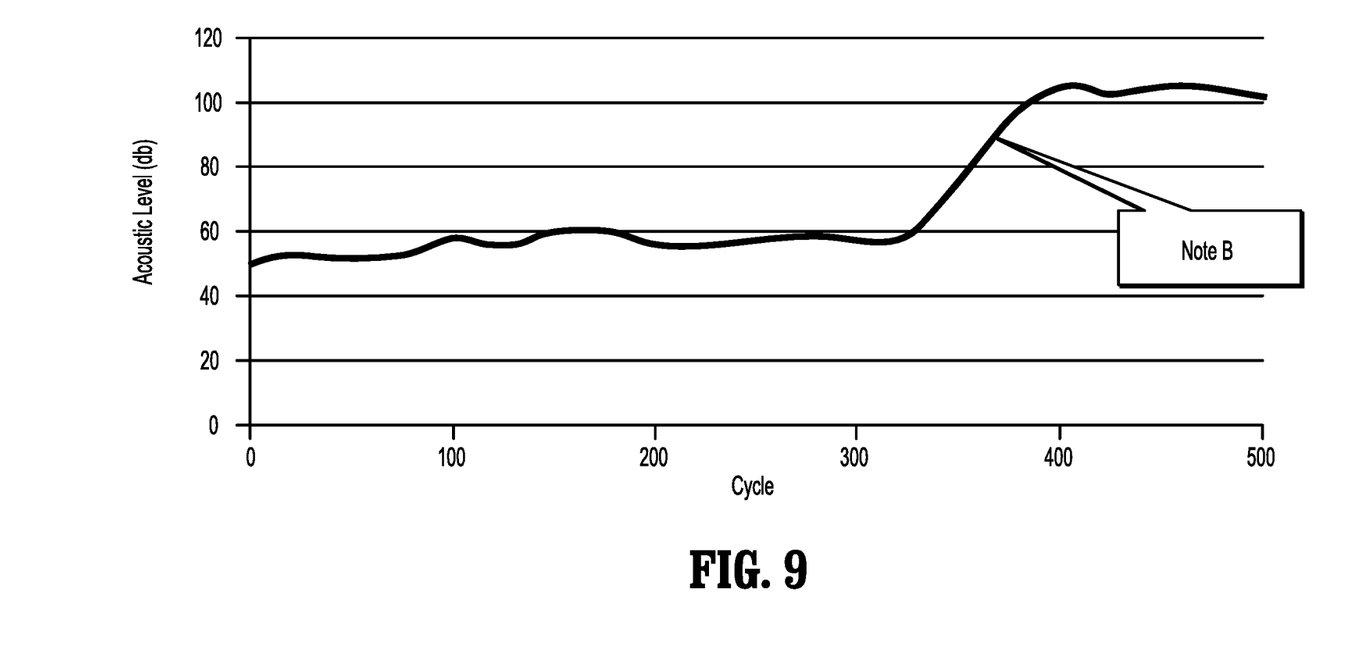
FIG. 9 is a chart depicting the collection of data to determine the end of life state of an instrument in accordance with an embodiment of the present disclosure.

FIG. 9 depicts an example of aggregating field data to set a threshold value. As shown in FIG. 9, acoustic data can be recorded by a device as it is used. This data can be monitored by the device for one or more triggering events which can include the passing of a set hard limit, or the occurrence of a sudden increase in a measured reading. (See Note B in FIG. 9.) This information can be used to anticipate a failure and facilitate a "safe failure" situation. In some embodiments, this technique can be applied in reverse to extend the lifespan of a device. For example, instead of simply limiting device life to 300 cycles this technique can leave the end of life open ended. If a device is performing well it can decide independently that it does not need to limit itself to 300 uses.

The performance of instrument 12 and/or its components is only one type of data that may be aggregated to determine the threshold value of the instrument 12. Other data that may be used include: (i) metrics based on geographic or hospital conditions; (ii) user or clinician metrics; and (iii) regional, geographic, or time zone based performance metrics. The metrics may be used to determine the end of life of the instrument 12 or adjust the operating parameters of the instrument 12. These metrics may be analyzed by the instrument 12, the dock 44, local server 48, or external server 50.

It will be understood that various modifications may be made to the embodiments disclosed herein. For example, surgical instrument 100 and/or cartridge assembly 410 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed is:

1. An electromechanical surgical system, comprising:
   an end effector configured to perform at least one function;
   a shaft assembly being arranged for selectively interconnecting the end effector and a hand-held surgical instrument, the hand-held surgical instrument including an instrument housing defining a connecting portion for selectively connecting with the shaft assembly;
   a motor assembly;
   a sensor array configured to:
      obtain at least one electrical metric of the hand-held surgical instrument; and
      measure at least one acoustic metric of the hand-held surgical instrument during an operation of the hand-held surgical instrument; and
   a controller configured to control operation of the hand-held surgical instrument based on the electrical metric obtained by the sensor array.

2. The electromechanical surgical system of claim 1, wherein the hand-held surgical instrument includes a transceiver configured to communicate with an external device.

3. The electromechanical surgical system of claim 2, wherein the external device is at least one of a charging device, a local sever, or an external server.

4. The electromechanical surgical system of claim 3, wherein the hand-held surgical instrument communicates with the charging device, the local server, or the external server via a cloud.

5. The electromechanical surgical system of claim 1, wherein the sensor array includes at least one acoustic sensor, temperature sensor, voltage sensor, current sensor, or vibration sensor.

6. The electromechanical surgical system of claim 1, wherein the controller compares the measured at least one acoustic metric against an acoustic threshold value associated with an end of life of the hand-held surgical instrument.

* * * * *